United States Patent
Iguchi et al.

(10) Patent No.: US 10,653,890 B2
(45) Date of Patent: May 19, 2020

(54) LIGHT IRRADIATION APPARATUS

(71) Applicant: SHARP KABUSHIKI KAISHA, Sakai, Osaka (JP)

(72) Inventors: Katsuji Iguchi, Sakai (JP); Jun Mori, Sakai (JP); Tohru Nakanishi, Sakai (JP)

(73) Assignee: SHARP KABUSHIKI KAISHA, Sakai, Osaka (JP)

( * ) Notice: Subject to any disclaimer, the term of this patent is extended or adjusted under 35 U.S.C. 154(b) by 0 days.

(21) Appl. No.: 15/553,850

(22) PCT Filed: Jan. 22, 2016

(86) PCT No.: PCT/JP2016/051933
§ 371 (c)(1),
(2) Date: Aug. 25, 2017

(87) PCT Pub. No.: WO2016/136349
PCT Pub. Date: Sep. 1, 2016

(65) Prior Publication Data
US 2018/0015298 A1    Jan. 18, 2018

(30) Foreign Application Priority Data

Feb. 26, 2015 (JP) ................................. 2015-036924

(51) Int. Cl.
| | | |
|---|---|---|
| *A61N 5/00* | (2006.01) | |
| *A61N 5/06* | (2006.01) | |
| *A61B 18/00* | (2006.01) | |

(52) U.S. Cl.
CPC ............. *A61N 5/0616* (2013.01); *A61N 5/06* (2013.01); *A61B 2018/00648* (2013.01);
(Continued)

(58) Field of Classification Search
CPC ...... A61N 5/0616; A61N 5/06; A61N 5/0613; A61N 2005/0652; A61N 2005/0661
See application file for complete search history.

(56) References Cited

U.S. PATENT DOCUMENTS 4,750,482 A * 6/1988 Sieverding .............. A61L 15/58
604/317
5,616,140 A    4/1997 Prescott
(Continued)

FOREIGN PATENT DOCUMENTS

JP    2008-253337 A    10/2008
JP    2008253337 A  *  10/2008
(Continued)

OTHER PUBLICATIONS

Kuniyuki Morimoto, et al.,'Photodynamic Therapy Using Systemic Administration of 5-Aminolevulinic Acid and a 410-nm Wavelength Light-Emitting Diode for Methicillin-Resistant *Staphylococcus aureus*-Infected Ulcers in Mice', PLOS One, Aug. 2014, vol. 9, Issue 8 e105173.

*Primary Examiner* — Michael W Kahelin
*Assistant Examiner* — Sana Sahand
(74) *Attorney, Agent, or Firm* — ScienBiziP, P.C.

(57) ABSTRACT

Provided is a simple light irradiation apparatus capable of performing uniform irradiation even on to a treatment area having a curved surface and capable of suppressing excessive heating caused by light irradiation. The light irradiation apparatus (10) includes a polymer gel layer (3) that covers the treatment area (2) on skin (1), an LED protective layer (6) that closely adheres to the polymer gel layer (3), and a substrate (5) on which LEDs (4) closely adhered to the LED protective layer (6) are arranged thereon. A current control apparatus (8) which lights the LEDs (4) controls irradiation intensity and stops irradiation when reaching a demanded dose amount.

11 Claims, 10 Drawing Sheets

(52) U.S. Cl.
CPC ... *A61B 2018/00821* (2013.01); *A61N 5/0624* (2013.01); *A61N 2005/002* (2013.01); *A61N 2005/005* (2013.01); *A61N 2005/007* (2013.01); *A61N 2005/0626* (2013.01); *A61N 2005/0627* (2013.01); *A61N 2005/0628* (2013.01); *A61N 2005/0632* (2013.01); *A61N 2005/0643* (2013.01); *A61N 2005/0652* (2013.01); *A61N 2005/0661* (2013.01); *A61N 2005/0663* (2013.01)

(56) References Cited

U.S. PATENT DOCUMENTS

| | | | |
|---|---|---|---|
| 5,913,883 | A | 6/1999 | Alexander et al. |
| 6,290,713 | B1 * | 9/2001 | Russell ................ A61N 5/0616 607/88 |
| 6,743,249 | B1 * | 6/2004 | Alden ................... A61N 5/0601 606/1 |
| 2006/0206173 | A1 * | 9/2006 | Gertner ............... A61N 5/0616 607/88 |
| 2006/0235346 | A1 * | 10/2006 | Prescott .............. A61N 5/0616 602/2 |
| 2007/0233208 | A1 * | 10/2007 | Kurtz .................. A61N 5/0613 607/88 |
| 2010/0106077 | A1 | 4/2010 | Rabin et al. |
| 2013/0144364 | A1 | 6/2013 | Wagenaar et al. |
| 2014/0276247 | A1 * | 9/2014 | Hall ..................... A61N 1/0432 601/2 |
| 2015/0165231 | A1 * | 6/2015 | Scheja .................... A61F 7/02 604/20 |
| 2016/0310140 | A1 * | 10/2016 | Belson .................. A61H 23/02 |

FOREIGN PATENT DOCUMENTS

| | | | |
|---|---|---|---|
| JP | 2008253337 | A * | 10/2008 |
| JP | 2010-246754 | A | 11/2010 |
| JP | 2010246754 | A | 11/2010 |
| JP | 2010246754 | A * | 11/2010 |
| WO | 0114012 | A1 | 3/2001 |
| WO | 2008144157 | A1 | 11/2008 |
| WO | 2012023086 | A1 | 2/2012 |

* cited by examiner

LIGHT IRRADIATION APPARATUS

TECHNICAL FIELD

The present invention relates to a light irradiation apparatus mainly for irradiating treatment areas of human and animal skin for treatment and barber beauty with light beams.

BACKGROUND ART

In general, light treatment is used for various purposes such as treatment of diseases such as neonatal jaundice, psoriasis, and acne, relief to pain and beauty. Green light beams and blue-white light beams are used for treatment of the neonatal jaundice, ultraviolet light is used for psoriasis treatment, and blue light beams, red light beams, and yellow light beams are used for acne treatment. In addition, various light sources are used depending on the application.

For example, in a case of using a light source such as an excimer lamp and an arc lamp, a treatment area is disposed at a certain distance from a fixed light source and irradiated with the light beams. However, since the light beams also hit on an area other than the treatment area in this method, it is demanded to take measures such as covering the area other than the treatment area with a light shielding object such as an eye mask for protecting the eyes. In addition, for curved parts such as hands and legs, since irradiation intensity varies depending on a location of the treatment area due to an angle and distance to the light source, it is difficult to uniformly irradiate the treatment area with the light beams. Furthermore, since such a lamp type apparatus is large and many auxiliary apparatuses such as a power supply and a cooling apparatus are demanded, a large installation space is demanded and price is high.

In addition, in a case where a light source such as a laser is used, since the light beams irradiated to the treatment area becomes spot light beams, it is demanded that the spot light beams are scanned in order to irradiate the treatment area of a large area with the light beams, so that an apparatus becomes complicated and expensive.

Furthermore, in a case where an apparatus that irradiates a surface with the light beams by utilizing an optical fiber is used, since efficiency of transmitting the light beams to the optical fiber is relatively low, irradiation power tends to be lowered, and thus it is suitable for only a relatively long treatment.

From the background as described above, there is a demand for a flexible light source for light beam treatment which can cover the treatment area while keeping a certain distance along the treatment area.

Here, a light-emitting diode (LED) is relatively smaller than other light sources, and it is possible to irradiate the treatment area having a curved surface with the different numbers of elements and different arrangement and the like with the light beams.

Therefore, with respect to the demand, the following PTLs using LEDs as the light-emitting sources are disclosed.

In PTL 1, a light irradiation apparatus in which a laser and an LED as the light-emitting source are disposed on a flexible substrate and which winds around the treatment area to be used is disclosed.

In PTL 2, a light irradiation apparatus for a face in which an LED as the light-emitting source is disposed on a flexible substrate and which covers the face in use is disclosed.

In PTL 3, a flexible light irradiation apparatus in which a large number of LEDs serving as a light-emitting source are arranged on a flexible substrate and which is wrapped around the treatment area, irradiating the wrapped treatment area with the light beams is disclosed.

In PTL 4, on the premise of application to the head, a light irradiation apparatus in which an LED serving as the light-emitting source is disposed inside a cap is disclosed.

In PTL 5, a light irradiation apparatus in which an LED serving as the light-emitting source is disposed of a flexible substrate and a light-transmitting material is interposed between the treatment area and the LED such that heat generated from the LED is transmitted to the treatment area is disclosed.

In NPL 1, a methicillin-resistant *Staphylococcus aureus* (MRSA) infection skin ulcer treatment method using LED near-ultraviolet light is described.

CITATION LIST

Patent Literature

PTL 1: U.S. Pat. No. 5,616,140 (issued on Apr. 1, 1997)
PTL 2: U.S. Pat. No. 5,913,883 (issued on Jun. 22, 1999)
PTL, 3: International Publication No. 01/14012 (published on Mar. 1, 2001)
PTL 4: International Publication No. 2008/144157 (published on Nov. 27, 2006)
PTL 5: International Publication No. 2012/023086 (published on Feb. 23, 2012)

Non Patent Literature

NPL 1: Kuniyuki Morimoto, 6 others, "Photodynamic Therapy Using Systemic Administration of 5-Aminolevulinic Acid and a 410-nm Wavelength Light-Emitting Diode for Methicillin-Resistant *Staphylococcus aureus*-Infected Ulcers in Mice", PLOS ONE, August 2014, Volume 9, Issue 8 e105173, (Published Aug. 20, 2014)

SUMMARY OF INVENTION

Technical Problem

However, the above-described related arts have the following problems.

In light treatment, it is demanded to be able to uniformly irradiate the treatment area with a demanded minimum amount of light beams. Excessive irradiation may cause side effects such as "sunburn" in the treatment area, and if the amount of irradiation is insufficient, treatment effect cannot be expected. This is also applied to an area having a curved surface such as an arm and a foot in the same manner. In order to uniformly irradiate the treatment area on the curved surface with light beams, it is demanded to arrange a flexible light source which can flexibly follow the curved surface while always keeping a fixed distance from the treatment area.

Although the light irradiation apparatus disclosed in each of PTLs 1 and 2 can flexibly irradiate the curved surface of the treatment area with the light beams, it is difficult to dispose the light irradiation apparatus at a certain distance from the treatment area at all times due to a structure of the light irradiation apparatus.

Although the efficiency of the LED is improved, a majority of the input electric power is dissipated as heat. In the light irradiation apparatus not having the cooling apparatus disclosed in each of PTLs 1, 2, and 4, there is a possibility that excessive heat is applied to the treatment area.

Therefore, some heat accumulation mechanisms or cooling mechanisms are demanded such that this heat does not adversely affect the treatment area. However, providing the cooling mechanism in the irradiation apparatus as disclosed in PTL 3 usually complicates the mechanism, causes cost increase, and loses flexibility of an irradiation area.

The present invention has been made in view of the above problems, and an object of the present invention is to provide a light irradiation apparatus which can uniformly irradiate a treatment area having a curved surface with light beams and which has a simple structure capable of suppressing excessive heating by light irradiation.

Solution to Problem

In order to solve the problem, there is provided a light irradiation apparatus according to the present invention for irradiating a treatment area with light beams, including light-emitting diodes that generate the light beams; and a polymer layer that contains water. The polymer gel layer has a contact surface which directly or indirectly adheres to the treatment area, and is formed on the light-emitting diodes with an approximately constant thickness.

Advantageous Effects of Invention

According to one embodiment of the present invention, it is possible to uniformly irradiate a treatment area having a curved surface with a light irradiation apparatus having a simple structure, and to suppress excessive heating by light irradiation.

DESCRIPTION OF EMBODIMENTS

Figure 1:
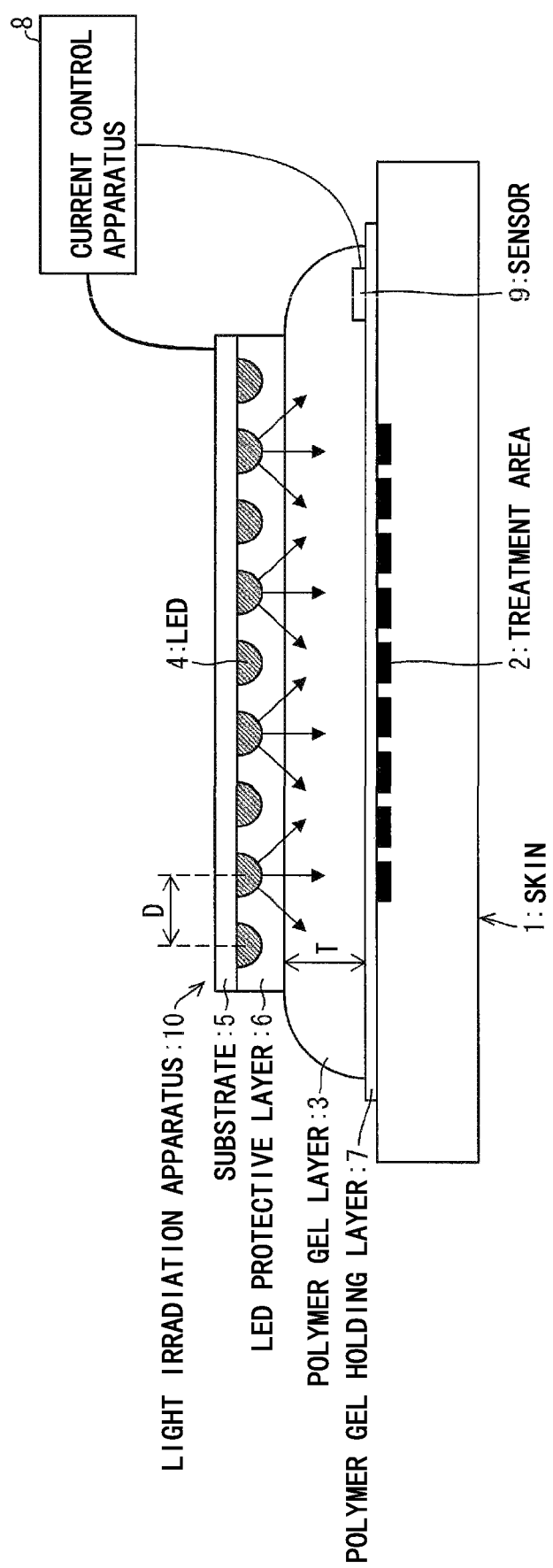
FIG. 1 is a sectional view showing a configuration of a light irradiation apparatus according to an embodiment 1 of the present invention.

An embodiment of the present invention will be described based on FIG. 1 to FIG. 10. Hereinafter, for convenience of explanation, the same reference numerals are given to the components having the same functions as those described in the specific embodiment, and the description thereof may be omitted in some cases.

Embodiment 1

Figure 2:
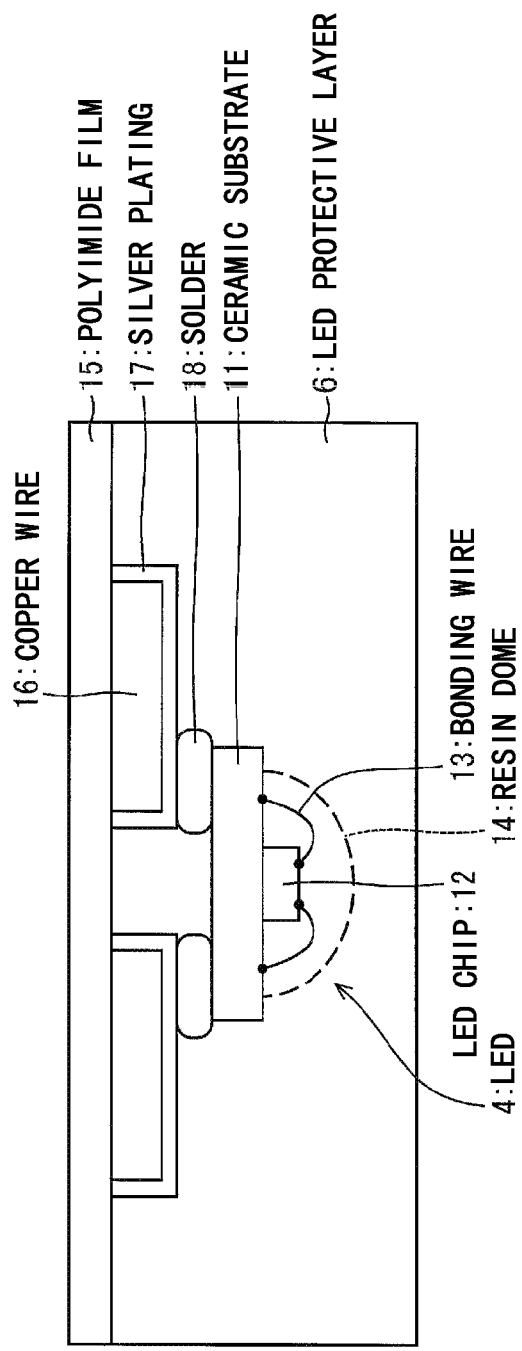
FIG. 2 is an enlarged sectional view showing a configuration of a part including an LED of the light irradiation apparatus in FIG. 1.
Figure 3:
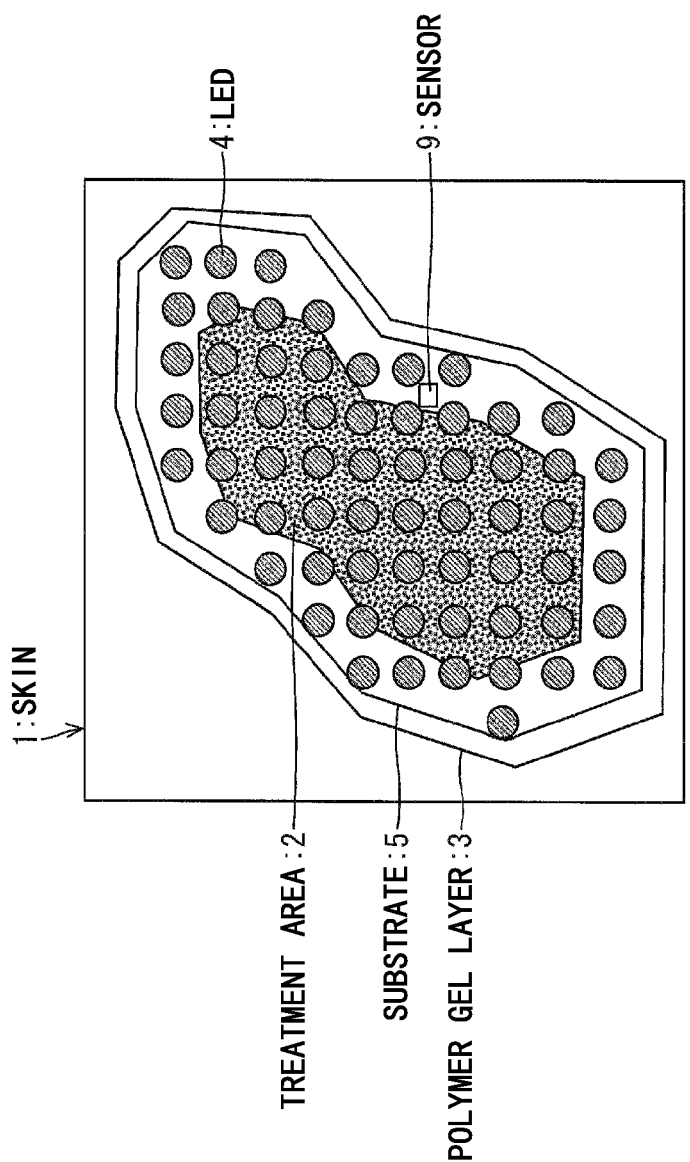
FIG. 3 is a plan view showing an arrangement of LEDs with respect to a treatment area of the light irradiation apparatus in FIG. 1.

Based on FIG. 1 to FIG. 4, a light irradiation apparatus 10 according to an embodiment 1 of the present invention will be described. FIG. 1 is a sectional view showing a configuration of the light irradiation apparatus 10 according to the embodiment 1. FIG. 2 is an enlarged sectional view showing a configuration of a part including an LED 4 of the light irradiation apparatus 10. FIG. 3 is a plan view showing an arrangement of LEDs 4 of the light irradiation apparatus 10 with respect to a treatment area 2.

As shown in FIG. 1, the light irradiation apparatus 10 according to the present embodiment includes a polymer gel layer 3 covering the treatment area 2 of skin 1, a light-emitting diode (hereinafter, referred to as LED) 4 as a light source closely adhered to the polymer gel layer 3, a substrate 5 on which the LED 4 is mounted, and a light-emitting diode protective layer (hereinafter, referred to as LED protective layer) 6 that covers the substrate 5 on a surface on which the LED 4 is mounted. In addition, the light irradiation apparatus 10 includes a current control apparatus 8 that turns on the LED 4 and a sensor 9 that detects light irradiation intensity and a temperature. The current control apparatus 8 (energization control unit) controls the irradiation intensity based on a temperature signal and a light amount signal from the sensor 9 installed on the skin 1, and can stop the irradiation of light beams when reaching the demanded dose amount. The sensor 9 may be installed on the substrate 5 instead of on the skin 1 as long as sensor 9 is a sensor having only a light irradiation intensity detection function.

LED 4 and Substrate 5

The LEDs 4 are mounted on the substrate 5 (on plane) at approximately even intervals. The LEDs 4 have to selected according to the purpose of treatment. Here, in order to be applied to "methicillin-resistant *Staphylococcus aureus* infection (MRSA) infected skin ulcer treatment", an LED (peak wavelength of 410 nm) emitting a gallium nitride type blue violet light beam is used. For other applications, an optimal LED 4 such as an ultraviolet LED, a blue LED, or a green LED of a gallium nitride (AlInGaN) LED, a red LED, a yellow LED, or a green LED of a quaternary (AlGaInP) LED, and a GaAs based infrared LED can be selected for purposes. In addition, it is also possible to combine a plurality of LEDs 4 of different wavelength ranges.

Various modes of the LED 4 and the substrate 5 on which the LED 4 is mounted can be adopted. Here, as shown in FIG. 2, two LED chips 12 emitting blue violet light beams and having a size of 440 μm×550 μm and a thickness of approximately 100 μm to 130 μm are mounted in series on a 2.8 mm square alumina ($Al_2O_3$) type white ceramic substrate 11 and an LED element which is covered with a resin dome 14 made of a silicone resin is used as the LED 4. The LED chip 12 is adhered to the ceramic substrate 11 by a die bond paste (not shown), and is connected to an electrode (not shown) by a bonding wire 13.

Here, an average distance D which is an average value of distances between the centers of the adjacent LEDs 4 is preferably 3 mm or more and 20 mm or less, and more preferably 5 mm or more and 10 mm or less.

As shown in FIG. 2, the substrate 5 is formed of a material in which a copper wire 16 is formed on a polyimide film 15 and a surface of the copper wire 16 is configured by a silver plating portion 17 formed by silver plating. The silver plating portion 17 is used to increase reflectance of treatment light beams and to reduce the loss of light beams. On this substrate 5, the LED 4 is attached to the copper wire 16 by a solder 18. An LED protective layer 6 is made of the silicone resin and is formed to cover a surface of the substrate in order to suppress corrosion of the silver plating portion 17, to ensure insulation of the surface of substrate, and to ensure waterproofness.

The light irradiation apparatus 10 may include a protective case (not shown) for accommodating the LED 4 instead of the LED protective layer 6. The protective case has flexibility and is formed of a material which can suppress the corrosion of the silver plating portion 17, ensure the insulation of the surface of substrate and ensure the waterproofness, similar to the LED protective layer 6. With this, it is possible to ensure the waterproofness for the LED 4.

As shown in FIG. 1, the LEDs 4 are arranged so as to cover the treatment area 2. The substrate 5 also manufactured so as to cover the treatment area 2. Although a back surface (side opposite to the surface on which the LED 4 is mounted) of the substrate 5 is in contact with air, it is preferable to let the heat generated by the LED 4 escape efficiently to the outside. By pasting a material having good conductivity through plating the entire back surface of the substrate 5 with copper, it is effective to spread the heat of the LED 4 to the whole of the substrate 5. In addition, it is preferable to increase the heat exhaust efficiency by adding unevenness on the back surface of the substrate 5. In applications with high heat generation, it is also possible to positively perform water-cooling by providing a cooling water pipe on the back side of the substrate 5.

Polymer Gel Layer 3

The polymer gel layer 3 is a gel layer containing water, which is formed in a plate shape by absorbing water into sodium polyacrylate granules. As long as it is a polymer having high water absorbability as sodium polyacrylate, other absorbent polymers can also be used. In addition to the polyacrylic acid salt type, various kinds of synthetic polymers such as polysulfonate type, maleic anhydride type, polyacrylamide type, polyvinyl alcohol type, and polyethylene oxide type, and water-absorbing polymers of natural origin such as polyaspartic acid type, polyglutamate type, polyalginate type, starch type, and cellulose type are known.

It is preferable that water is pure water, but any can be used if water has a small ion content such as tap water. In addition, as long as it is at a low concentration, it may be in a form of an aqueous solution to which known agents are added. As a result, the polymer gel layer 3 contains a drug component. In order to facilitate the handling of the polymer gel layer 3, it is preferable to cover a lower surface (surface adhered to treatment area 2) with a polymer gel holding layer 7 which is a transparent film that passes through the light beams of an effective wavelength range for treatment. The polymer gel holding layer 7 may cover both upper and lower surfaces. For example, as the effective wavelength range for treatment, in a case of using the blue-violet LED, it is preferably 400 nm or more and 430 nm or less, and more preferably 380 nm or more and 450 nm or less. Alternatively, in a case where another LED as the effective wavelength range for treatment is used, it is desired that the wavelength range is ±20 nm with respect to the peak wavelength, and more preferably it is transparent in a range of approximately ±30 nm.

The polymer gel layer 3 has a contact surface that directly adheres to the treatment area 2, and thus it is preferable to completely cover the treatment area 2. However, the polymer gel layer 3 may not directly adhere to the treatment area 2 but may indirectly adhere to the treatment area 2. For example, a thin film may be interposed between the polymer gel layer 3 and the treatment area 2, or the polymer gel layer 3 may adhere to the treatment area 2 after applying cream or the like on the treatment area 2. Since most of the treatment light beams are confined in the polymer gel layer 3, an area not covered with the polymer gel layer 3 is hardly irradiated with the light beams. Therefore, the treatment area 2 to be treated needs to be covered with the polymer gel layer 3. In order to perform light irradiation with sufficient intensity for treatment, it is preferable to cover an area indicated by an outline which is a certain distance away from an area indicated by an outline surrounding the treatment area 2 in FIG. 3.

Most of the polymer gel layer 3 is water and water absorbs heat from the light beams, so that overheating of the treatment area 2 by the light beams can be suppressed. Without the polymer gel layer 3, the heat generated by light absorption at the treatment area 2 had to be cooled with blood flowing in the body. However, due to the polymer gel layer 3, exhaust heat for a surface side of the treatment area 2 can be expected. From the viewpoint of cooling effect, the polymer gel layer 3 is preferably thicker. Although thicker one makes the light irradiation intensity uniform, there is a case where the thickness is limited based on a shape of the treatment area 2. Although a thickness T of the polymer gel layer 3 depends on the treatment area 2 which is an irradiation target, it is preferably, for example, 1 mm or more and 20 mm or less, and more preferably 3 mm or more and 12 mm or less.

In addition, by cooling the polymer gel layer 3 before irradiation with the light beams to lower the temperature, it is possible to lengthen a light irradiation time. For example, in a case where the maximum allowable temperature is 40° C. and room temperature is 25° C., an allowable range of temperature increase can be expanded from approximately 15° C. to approximately 30° C. by cooling the polymer gel layer 3 to 10° C. In the present embodiment, the polymer gel layer 3 is cooled to 10° C. and then irradiation with the light beams is performed. The temperature to which the polymer gel layer 3 is cooled depends on the treatment area 2 which is the irradiation target, the maximum allowable temperature, and the like, but it is preferably cooled to, for example, 0° C. or more and 20° C. or less, and more preferably 5° C. or more and 15° C. or less.

The thickness T of the polymer gel layer 3 is an important parameter for evenly irradiating the treatment area 2 with the light beams. It is preferable that $0.5 \leq T/D$, and more preferably $0.8 \leq T/D$, with respect to an average distance D between respective LEDs 4. As a result, since the thickness of the polymer gel layer 3 is not too thin with respect to the distance between the LEDs 4, problems occurring when the polymer gel layer 3 is too thin can be suppressed. In other words, a problem that when the polymer gel layer 3 is thin, the treatment area 2 becomes close to the LED 4, and the treatment area close to the LED 4 is irradiated with a large amount of light beams, while the treatment area away from the LED 4 is irradiated with a small amount, can be suppressed.

Sensor 9

A sensor 9 monitors the temperature and/or irradiation light intensity of the treatment area 2. If the light irradiation for the treatment area 2 is not affected, known technologies can be used. However, the sensor 9 is demanded to have water resistance.

In many cases, an irradiation light intensity sensing function of the sensor 9 can be omitted. The output of the LED 4 is stable, and if relationship between the output and the light intensity is calibrated in advance, predetermined irradiation intensity can be obtained by flowing a designated current and an amount of demanded dose in time control can be irradiated. In this case, instead of using a temperature sensor as the sensor to control a current amount by the current control apparatus 8, the irradiation with beams is interrupted, by turning ON and OFF a current, such that the temperature does not exceed the predetermined temperature. As a result, the treatment area 2 and the skin 1 surrounding the treatment area 2 are enabled to avoid getting hot.

Here, in a case where temperature measurement is performed in advance in accordance with an actual irradiation situation and the temperature increase is suppressed within the allowable range, the temperature monitoring can be omitted. In a case where the total irradiation amount is small and the temperature is kept at 40° C. or less even at the end of irradiation, in a case where average irradiation power is low and the temperature does not rise to or more, in a case where average irradiation power is kept low by pulse driving and the temperature does rise to 40° C. or more even if the continuous irradiation is performed, or the like, no temperature monitoring is demanded. In an emergency case where such preliminary evaluation cannot be made, it is preferable to use the sensor 9.

With regard to setting the upper limit temperature to 40° C., it is generally indicated that there is no burn in irradiation for several ten minutes if the temperature is set to this degree, but the upper limit temperature may be further lowered depending on the situation. On the contrary, if in a short time, there is also a case where temperature increase can be tolerated a little more. Although the upper limit temperature depends on the treatment area 2 which is the irradiation target, it is preferably, for example, 51° C. or less, and more preferably 44° C. or less.

Current Control Apparatus 8

In the simplest form, the current control apparatus 8 is a constant current source that supplies a constant current to an LED element group, and controls an optical dose amount by setting a current supply time as a timer. In a case of using the temperature sensor, control is performed that the upper limit of the temperature set, the energization is stopped when approaching the upper limit temperature (for example, 40° C. (certain temperature)), the energization is started again when the temperature decreases, the power source is turned off when the total irradiation time reaches the set time, and termination is notified. The light irradiation time depends on the treatment area 2 which is the irradiation target, but it is preferably, for example, 30 minutes or less, and more preferably 15 minutes or less. In a case (for example, in a case where the sensor 9 is used) where the temperature monitoring and light irradiation intensity monitoring are used together, control is performed so that the upper limit temperature and the demanded dose amount are set, and the irradiation is terminated and the termination is notified when reaching the demanded dose amount while controlling the current so as not to reach the upper limit temperature. As the light irradiation intensity on the treatment area 2 which is the irradiation target, for example, it is preferably 10 mW/cm$^2$ or more and 200 mW/cm$^2$ or less, and more preferably 50 mW/cm$^2$ or more and 150 mW/cm$^2$. The demanded dose amount depends on the treatment area 2 which is the irradiation target, for example, it is preferably 40 J/cm$^2$ or more and 65 J/cm$^2$ or less, more preferably 45 J/cm$^2$ or more and 55 J/cm$^2$ or less.

In the simplest case, if all the LEDs 4 is connected in series, the same current can be supplied to all the LEDs 4, and approximately the same output can be obtained from each of the LEDs 4. However, in a case where the number of LEDs 4 is large, the voltage may be too high if all are connected in series. That is, a plurality of lines in which approximately the same number of LEDs 4 are connected in series are provided, and in this case, it is demanded to mount a plurality of constant current power supplies capable of outputting the same current. In FIG. 3, 64 LEDs are mounted, and in a case where 100 mA flows through each element, a voltage of approximately 6.2 V is demanded for each element. As a result, in series connection, a high voltage of approximately 400 V in total is demanded, and the danger is high. For this reason, two lines of wires in which 32 LEDs are connected in series are provided and two identical power sources of 200 V series are used such that each element can be energized with 100 mA.

Effect Verification

In the present embodiment, the light irradiation apparatus of the present embodiment was applied to light treatment in which the ulcer formed on the pig's back was infected with methicillin-resistant *Staphylococcus aureus* (MRSA), and systemic administration of 5-aminolevulinic acid (ALA) and blue violet light beams with a wavelength of 410 nm were used. ALA is partially converted into protoporphyrin IX (hereinafter, referred to as "PpIX") in the body of MRSA. PpIX is a photosensitizing substance and decomposed by the blue violet light beams, active oxygen generated upon decomposition attacks MRSA, and thus MRSA can be reduced. In addition, the cells themselves of the treatment area 2 are not adversely affected, and bacteria which have antibiotic resistance can be sterilized without causing antibiotic contamination.

In the present embodiment, an ulcer of approximately 50 mm×100 mm was formed on the back of each of two experimental and infected with MRSA. ARA was administered to one pig in advance and the light irradiation was performed in a rest state by causing the pig to sleep with a sleeping pill. Nothing is performed on the other pig. In this state, transition of the size of the ulcer was observed.

In the light irradiation, a substrate 5 on which 64 LEDs 4 emitting blue violet light beams are mounted was formed in accordance with a form (treatment area 2 in FIG. 3) of the ulcer as shown in FIG. 3. Two lines of wires in which 32 LEDs 4 are connected in series was provided such that the two lines of wires could be connected to constant current power sources of two lines which can be boosted up to 210 V, respectively. The average distance D between respective LED 4 elements is 10 mm.

A temperature sensor (sensor 9) and light intensity sensor (sensor 9) were attached to a normal area close to the treatment area 2. A thermocouple was used as the temperature sensor. A PN diode was used as the light intensity sensor. Calibration between an output inside the polymer gel layer 3 and the actual light intensity and temperature was performed in advance.

Pure water was absorbed in sodium polyacrylate granules, and the polymer gel layer 3 having a thickness of approximately 10 mm was manufactured, and disposed to cover the treatment area 2. It was set so that a distance from an end portion of the treatment area 2 to an end portion of the polymer gel layer 3 was approximately 10 mm to 20 mm. Next, the substrate 5 on which the LED 4 is mounted is closely adhered to the polymer gel layer 3 so that the LED 4 faces the treatment area 2. By laminating the polymer gel holding layer 7 which is a thin transparent film layer on a lower surface of the polymer gel layer 3, handling of the polymer gel layer 3 becomes easy. There was no great change in the light irradiation intensity on the skin 1.

Next, a current of 100 mA was applied to the two lines of wires for 8 minutes. It was checked that the light irradiation intensity measured by the light intensity sensor was approximately certain and there was an average irradiation intensity of approximately 104 mW/cm$^2$. From this, in order to achieve a target dose of approximately 50 J/cm$^2$, this energization time was determined to 8 minutes. It was checked that a monitored value of the temperature sensor increased by approximately 29° C. almost in proportion to a time from an initial temperature of 10° C. to 39° C. by the energization for 8 minutes. It is considered that there is no adverse effect due to temperature.

After the treatment described above on the pigs on which the light irradiation is performed, when the sizes of the ulcers of two pigs were observed, the ulcer of the pig that did not undergo the treatment did not shrink even if a predetermined time has elapsed. However, the ulcer of the pig irradiated with the light beams shrunk nearly uniformly on the entire surface of the treatment area 2 every day, and eventually disappeared. As described above, it is considered that MRSA could be killed almost evenly on the entire surface of the treatment area 2 by the light irradiation after administration of ALA.

Modification

Figure 4:
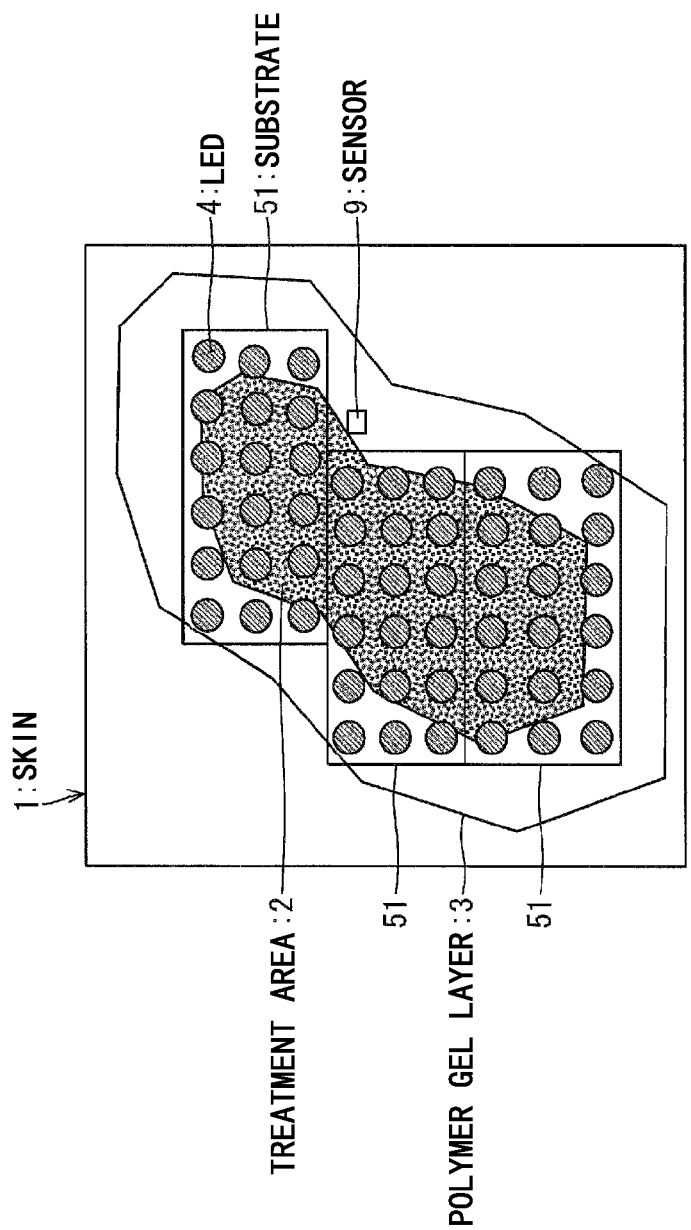
FIG. 4 is a plan view showing an arrangement of LEDs on a treatment area of a light irradiation apparatus according to a modification example of the embodiment 1 of the present invention.

Based on FIG. 4, the light irradiation apparatus 10 according to a modification example of the embodiment 1 will be described. FIG. 4 is a plan view showing the arrangement on the treatment area of LEDs of the light irradiation apparatus according to the modification example.

The modification example according to the present embodiment has the same configuration as the embodiment except that a shape of the substrate 5 and the arrangement of the LEDs 4 are different. Originally, the size and shape of the treatment area 2 are different for each of patients, and it is preferable to manufacture the substrate 5 so as to conform to the respective shape thereof, and arrange the LEDs 4. However, a substrate design, cost, and time are demanded to individually change the shape, which are not suitable for general treatment. On the other hand, although it is possible to form a larger substrate 5 so as to correspond to various treatment areas 2, unnecessary light irradiation may be applied to portions other than the treatment area 2, and the treatment cost also increases.

Therefore, in this modification example, substrates 5 of standardized size are used in combination. Specifically, as shown in FIG. 4, three substrates 51 on each of which LEDs 4 of 3×6=18 are mounted to be set the average distance D between respective LEDs 4 to 10 mm are combined to have 54 LEDs 4 in total. Compared to the embodiment 1, the number of the LEDs 4 covering the treatment area 2 is reduced, so that an area where the substrates 51 do not cover the treatment area 2 also occurs. However, by an optical confinement effect of the polymer gel layer 3, it is possible to irradiate the end portion of the treatment area 2 with light beams having sufficient intensity. The reason why such a plurality of substrates 51 can be used in combination is that the polymer gel layer 3 is interposed between the treatment area 2 and each of the substrates 51 to fix the treatment area 2 and the substrates 51 each other, and to equalize the irradiation intensity to some extent by confining the light beams.

By using the light irradiation apparatus 10 including such substrates 51, a result obtained by performing the light irradiation on the same treatment area 2 as that of FIG. 2 was verified.

In this modification example, three identical constant current power sources were combined, and 100 mA was supplied to each of the three substrates 51. A voltage of approximately 112 V was applied to each of the substrates.

When the experiment was performed in the same manner as described in embodiment 1, the irradiation time was 11 minutes. In this experiment, the sensor 9 was installed near the treatment area 2 not covered with the LED 4, and consideration was given such that a sufficient light dose could be given to such a treatment area 2. Since the number of the LEDs 4 installed outside the treatment area 2 is smaller than that in the embodiment 1, the light irradiation intensity for an outer peripheral portion of the treatment area 2 decreases. The uniformity of the light irradiation intensity seen on the whole area of the treatment area 2 becomes worse. However, in this treatment, if the demanded dose amount is exceeded, since a slight overdose does not cause a noticeable adverse effect on the treatment area, it is considered to be a reasonable choice in consideration of the time and cost of preparing a dedicated irradiation apparatus.

As a result of observing the size of the pig ulcer on which the light irradiation treatment is performed, the pig ulcer obviously shrunk every day and finally disappeared, similar to the case of embodiment 1. Even in the treatment area 2 which is not covered with the LED 4, since retraction of the ulcer was not particularly slow as compared with the other portion, it is considered that the light irradiation of a demanded amount could be performed on the entire surface of the treatment area 2 including such a treatment area 2 and MRSA could be killed.

Embodiment 2

Figure 5:
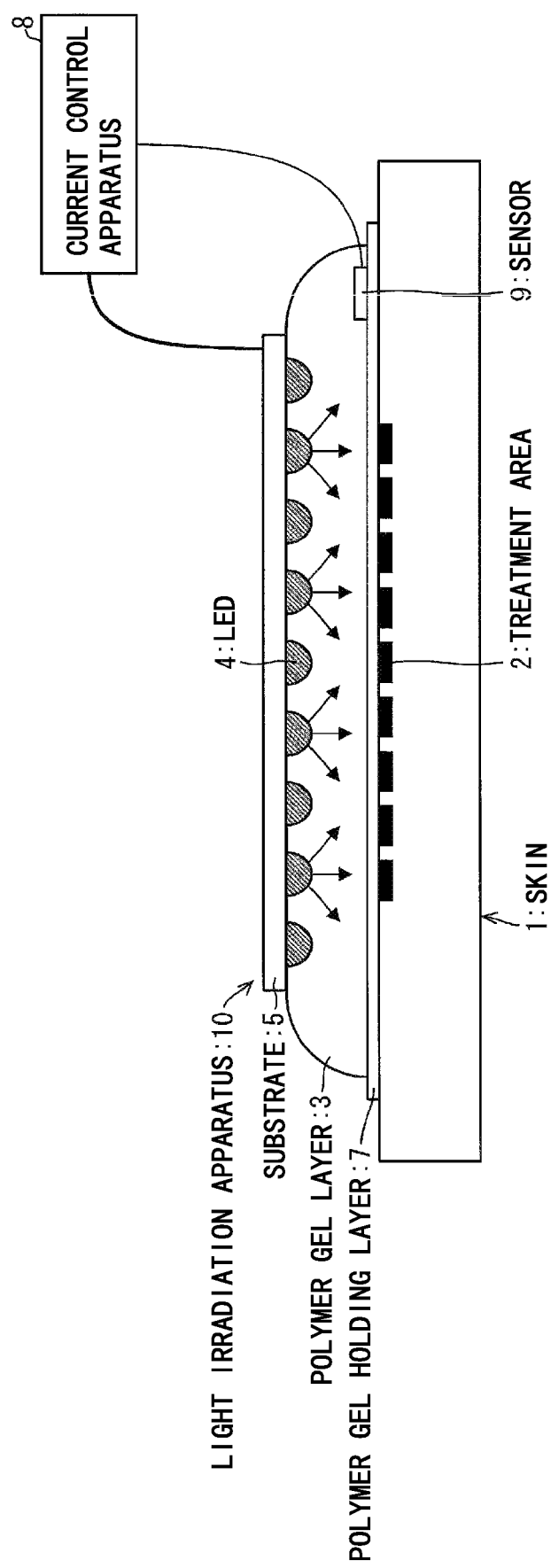
FIG. 5 is a sectional view showing a configuration of a light irradiation apparatus according to the embodiment 2 of the present invention.
Figure 6:
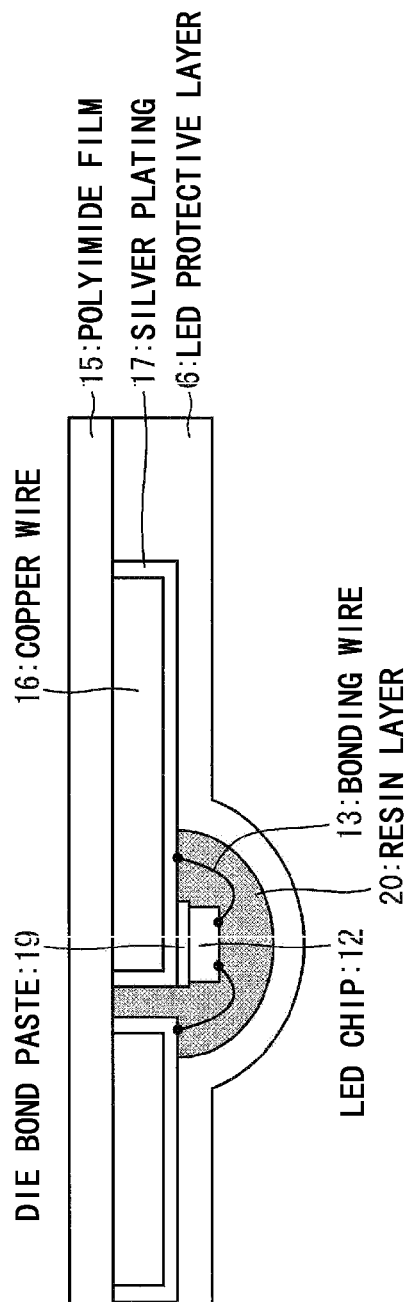
FIG. 6 is a detailed sectional view showing the configuration of the light irradiation apparatus in FIG. 5.

Based on FIGS. 5 to 6, a configuration of the light irradiation apparatus 10 according to an embodiment 2 of the present invention will be described. FIG. 5 is a sectional view showing a configuration of the light irradiation apparatus 10 according to the embodiment 2. FIG. 6 is a detailed sectional view showing the configuration of the light irradiation apparatus 10.

As shown in FIG. 5, the light irradiation apparatus 10 according to the present embodiment is different from the embodiment 1 in the configuration of the substrate 5 and the LED 4. As shown in FIG. 2, in the above-described embodiment 1 and the modification example thereof, the LED chip 12 is mounted on the ceramic substrate 11 and covered with the resin dome 14, and the ceramic substrate 11 is connected to the copper wire 16 through the solder 18.

In this structure, due to the thickness of the ceramic substrate 11 and the height of the resin dome 14, a mounting portion of the LED chip 12 becomes thick. As a result, a portion (substrate portion) configured by the LED 4, the substrate 5, and the LED protective layer 6 shown in FIG. 1 also became thick, and flexibility of the substrate portion was somewhat sacrificed. Therefore, it is desirable to increase the flexibility of the substrate portion with respect to the treatment area 2 having a larger curvature.

Therefore, in the light irradiation apparatus 10 of the present embodiment, the LED chip 12 is mounted on the polyimide film 15 without passing through the ceramic substrate 11 without using the resin dome 14. With such a form, although the durability is somewhat sacrificed, the flexibility increases.

Specifically, as shown in FIG. 6, the copper wire 16 is formed on the polyimide film 15 and the silver plating portion 17 is formed on a surface of the copper wire 16, similar to the embodiment 1.

The LED chip 12 is fixed to the copper wire 16 by a die bond paste 19, and an electrode on the LED chip 12 and the copper wire 16 on which the silver plating portion 17 is formed are connected to each other by the bonding wire 13.

A resin layer 20 is formed at portions of the LED chip 12 and the bonding wire 13 so as to be potted and covered by a silicone resin in order to protect the portion. Further thereon, in order to suppress corrosion of the silver plating portion 17 and ensure insulation of a surface of the polyimide film 15, the LED protective layer 6 formed of the silicone resin is formed so as to coat the surface. In a case where the LED protective layer 6 can be formed to embed a thickness enough to sufficiently fill the bonding wire 13, the resin layer 20 can be omitted.

In this structure, it is possible to form a relatively flat surface without using a thick coating material, it is hard for air to remain at a boundary surface of an adhered portion in the close adherence between the substrate portion and the polymer gel layer 3, the substrate portion can be easily placed on the treatment area 2, and thus the cost of the substrate portion can be reduced. In addition, since the flexibility of the substrate portion is high, this technique is also easily applied to the treatment area 2 having a larger curvature.

In this structure, as shown in FIG. 5, the LEDs 4 are arranged so as to be installed inside the polymer gel layer 3. Here, thickness variation of the LED chip 12 does not exceed ±10 μm, and the thickness of the polymer gel layer 3 is approximately 10 mm such that this variation can be practically negligible. As a result, since the thickness of the polymer gel layer 3 is steady and the sizes of the LEDs 4 are uniform, it is possible to irradiate the light beams while keeping a distance between the LED 4 and the treatment area 2 steady.

In the present embodiment, by using the substrate 5 in which 6×6=36 LED chips 12 are arranged in an array shape that the average distance D between the respective LEDs 4 is 7 mm, treatment was performed on the ulcer of approximately 20 mm formed on the forefoot of pig by the light irradiation apparatus. The LED chips 12 were wired to be connected in series, and emitted the light beams at 100 mA. The demanded voltage was approximately 126 V. In a sleep state of pigs after letting pigs take ALA, the polymer gel layer 3 of approximately 9 mm thick molded was attached the treatment area 2 to approximately 45 mm square, the LED substrate including the LED 4, the substrate 5 and the like was pushed down thereon, and the whole was wrapped in a bandage and fixed. The LED board was greatly curved, but energization was done without problems. The demanded irradiation time was 12 minutes. The temperature also rose 30° C. and under.

The size of the ulcer after irradiation shrunk every day and finally disappeared, similar to the embodiment 1. As described above, the treatment effect could be checked.

Embodiment 3

Figure 7:
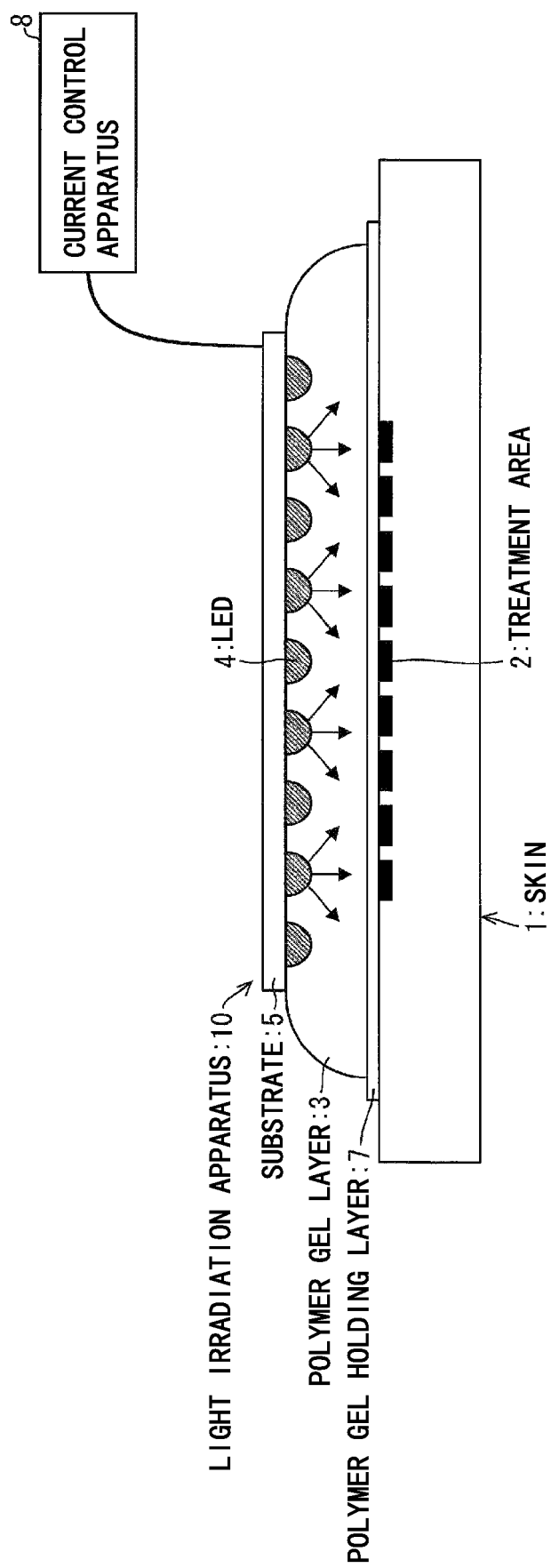
FIG. 7 is a sectional view showing a configuration of a light irradiation apparatus according to an embodiment 3 of the present invention.

Based on FIG. 7, a configuration of the light irradiation apparatus 10 according to an embodiment 3 of the present invention will be described. FIG. 7 is a sectional view showing the configuration of the light irradiation apparatus 10 according to the embodiment 3.

As shown in FIG. 7, the light irradiation apparatus 10 according to the present embodiment is different from the light irradiation apparatus 10 of the embodiment 2 in that the sensor 9 is not mounted.

By using the light irradiation apparatus as configured above, the irradiation intensity and the temperature increase are previously measured for the polymer gel layers 3 of various sizes, a drive current and an irradiation time which are optimum are considered, and thus the light treatment was performed by a simple current setting and timer control. The treatment effect was obtained without problems similar to the case where the sensor 9 is used. As a safety apparatus not causing had effects due to burns or overdose, the longest irradiation time which can be set for the drive current is determined such that the irradiation was controlled to stop at the longest irradiation time even if the set time is set long. The light irradiation was performed by a driving current of 100 mA and the irradiation time of 13 minutes. In addition, it was possible to check that a monitor value of the temperature sensor increased by approximately 32° C. in proportion to a time from an initial temperature as 10° C. to 42° C. by the energization for 13 minutes. It is considered that there is no adverse effect by the temperature.

In a case where the patient feels hot, the patient can operate an emergency stop switch such that the patient can stop the treatment immediately. By doing so, accidents can be suppressed in advance, the power source can be simplified, and overall cost can be reduced.

The size of the ulcer after irradiation shrunk every day and finally disappeared, similar to the embodiment 1. As described above, the treatment effect can be checked.

The present embodiment and the following embodiments 4 to 6 can be applied not only to the embodiment 2 but also to the embodiment 1.

Embodiment 4

Figure 8:
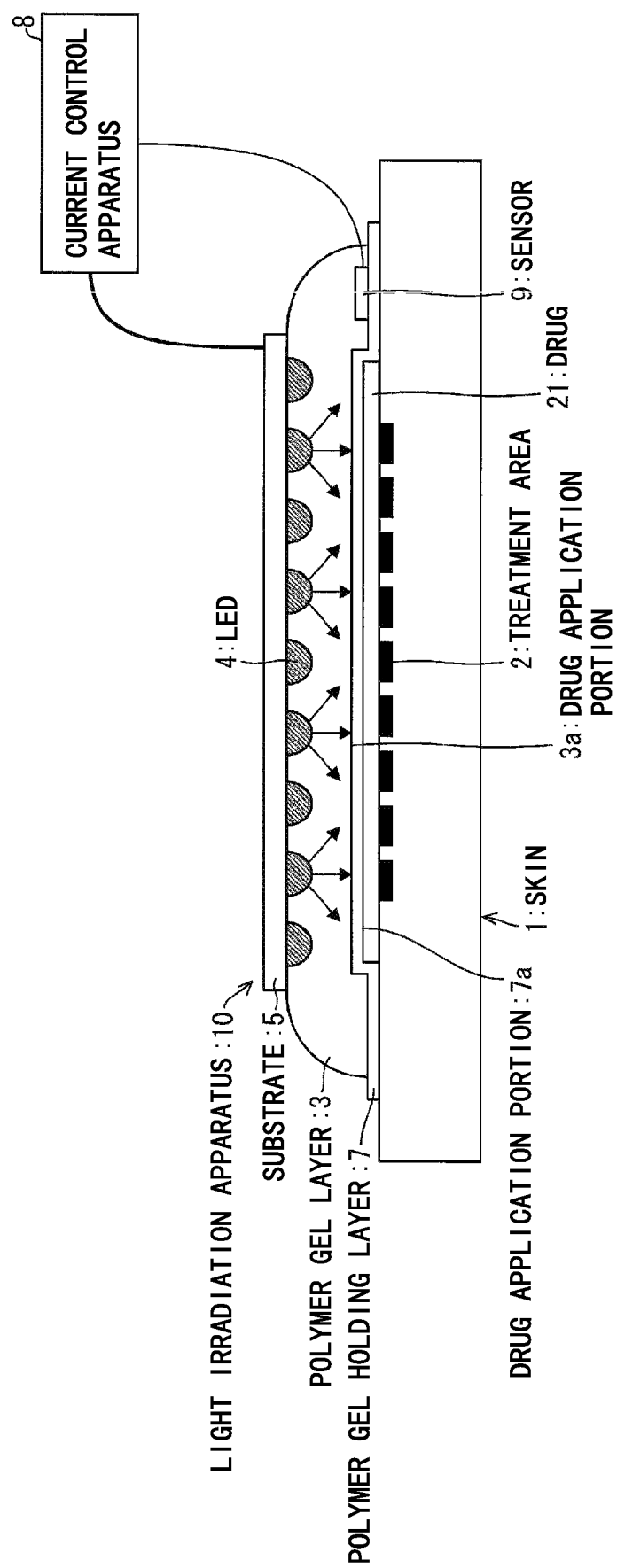
FIG. 8 is a sectional view showing a configuration of a light irradiation apparatus according to an embodiment 4 of the present invention.

Based on FIG. 8, a configuration of the light irradiation apparatus 10 according to an embodiment 4 of the present invention will be described. FIG. 8 is a sectional view showing a configuration of the light irradiation apparatus 10 according to the embodiment 4.

In the light irradiation apparatus 10 according to the embodiment, the light irradiation apparatus 10 according to the present embodiment is applied to acne treatment unlike the light irradiation apparatus 10 of the embodiment 2. In a case of the acne treatment, in general, treatment in which 20% aqueous solution of ALA or methyl aminolevulinate (MAL) is applied to the treatment area 2 and irradiated with blue light beams or red light beams for 15 to 20 minutes after leaving for approximately 3 hours is performed weekly once or twice. In the current light irradiation apparatus, there are many cases where the light irradiation is performed on the entire face by a large lamp shape light irradiation apparatus. In a case where there is acne on the front face, there is no solution. However, in a case where there is partially acne, if the light beams can be irradiated on only that portion, the load on the patient can be remarkably reduced.

Therefore, application of the present embodiment was attempted. As shown in FIG. 8, in the light irradiation apparatus 10, a drug 21 using MAL is applied to a drug application portion 7a on a contact area of the treatment area of the macromolecular gel holding layer 7 with respect to the acne on the cheek. Alternatively, in the light irradiation apparatus 10 not provided with the polymer gel holding layer 7, the drug 21 is applied to the drug application portion 3a on the contact surface of the treatment area of the polymer gel layer 3. At the time of using, after leaving for 3 hours after applying the medicament 21, the polymer gel layer 3 having a thickness of approximately 7 mm which had been cooled to 15° C. was affixed to the treatment area 2, and the substrate 5 used in the embodiment 1 or 2 was attached thereon, and thus the light irradiation was performed. However, this time, a blue LED chip 12 suitable for the acne treatment was used instead of the blue violet light beams. The blue LED chip 12 having a size of 440 μm×550 μm was used. It was a size on one substrate and the peak wavelength was 447 nm. 6×6=36 LED chips 12 was arranged in an array shape on the substrate 5 of 50 mm square so that the average distance D between respective LEDs 4 is 10 mm. Wires of two lines in which each line includes 18 LED chips connected in series were formed and a current of 50 mA flowed through each of them. An applied voltage was 58 V. Due to constraints of temperature increase, irradiation time was set to 5 minutes. Three irradiations were performed with a cooling time therebetween.

It was possible to check that the monitor value of the temperature sensor increased by approximately 25° C. in proportion to a time from an initial temperature as 15° C. to 40° C. by energization for 5 minutes. It is considered that there is no adverse effect by the temperature.

By this method, it was possible to easily perform local light irradiation. The effect was the same as light irradiation by a lamp of related arts.

In addition, for acne treatment, the red light beams can be used in the same manner. A red LED can also be used instead of the blue LED. In addition, it is also possible to mount the red LED and the blue LED, and it is possible to optimize each irradiation time and timing.

Embodiment 5

Figure 9:
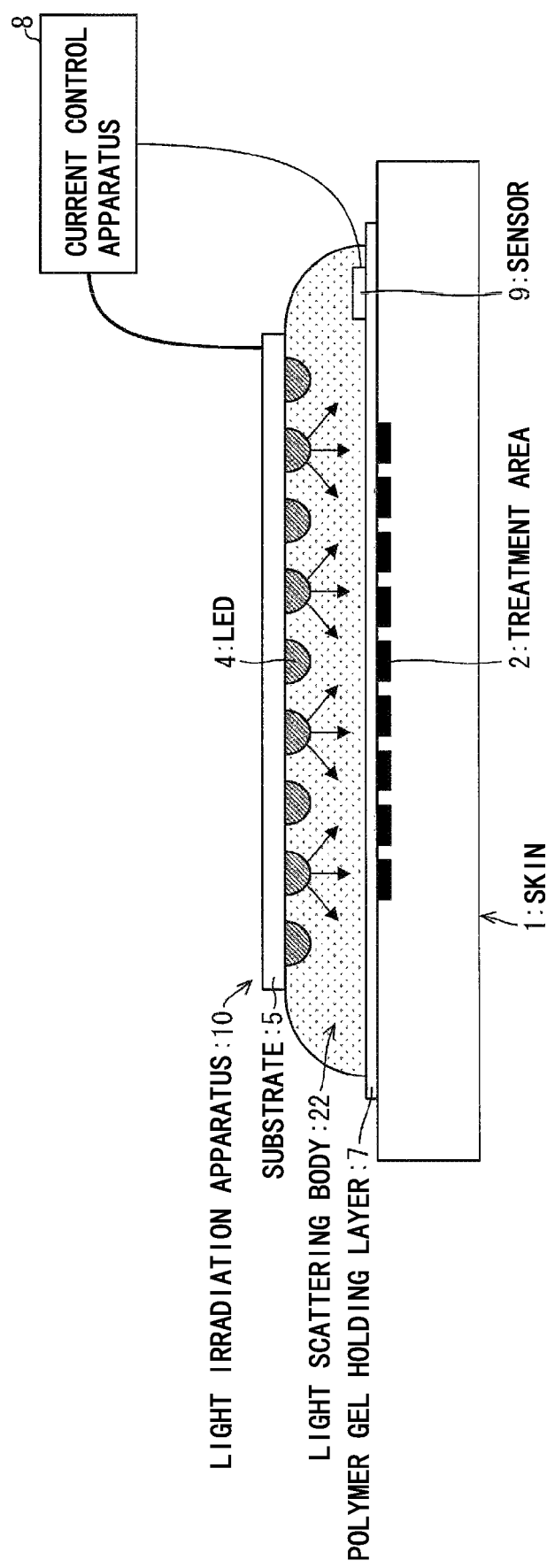
FIG. 9 is a sectional view showing a configuration of a light irradiation apparatus according to an embodiment 5 of the present invention.

Based on FIG. 9, a configuration of the light irradiation apparatus 10 according to an embodiment 5 of the present invention will be described. FIG. 9 is a sectional view showing a configuration of the light irradiation apparatus 10 according to the embodiment 5.

As shown in FIG. 9, the light irradiation apparatus 10 according to the present embodiment is different from the light irradiation apparatus 10 of the embodiment 2 in that a light scattering body 22 formed of fine particles of silica ($SiO_2$) are added to the polymer gel layer 3, as shown in FIG. 9. By increasing light scattering inside the polymer gel layer 3, the light irradiation intensity can be uniformed. In a case where there is no the light scattering body 22, the light intensity variation on the irradiated surface was 11%, but the light intensity variation could be reduced to 7% by adding the light scattering body 22.

Embodiment 6

Figure 10:
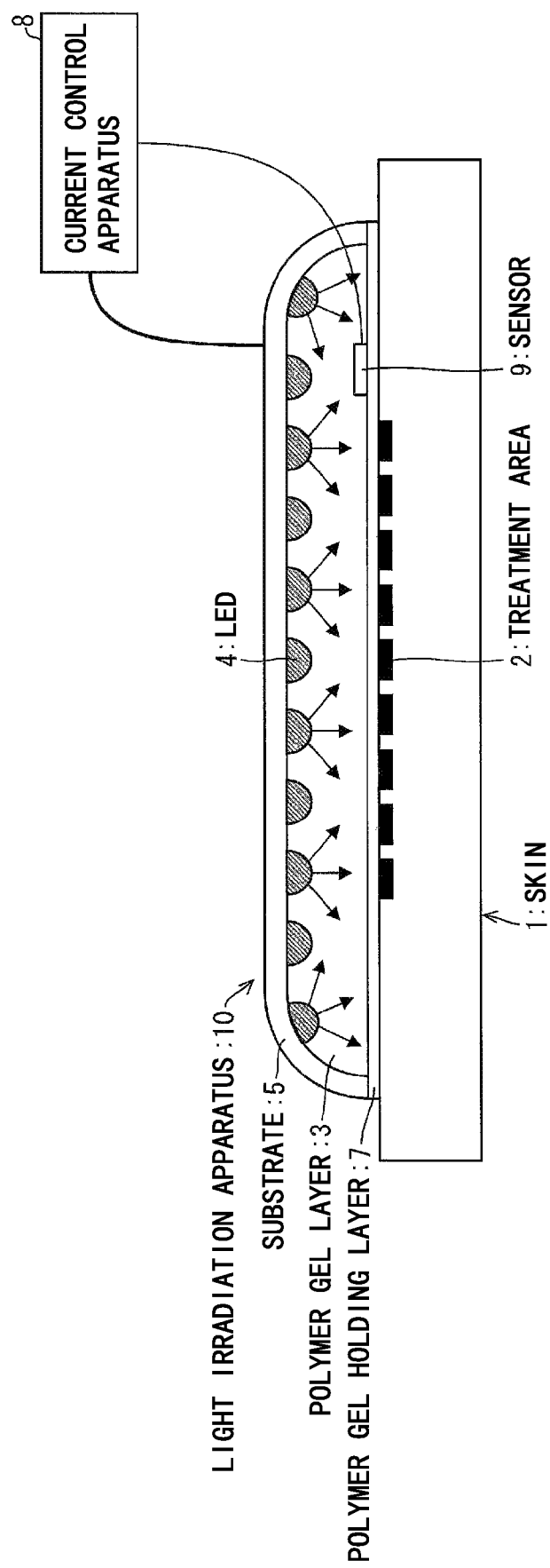
FIG. 10 is a sectional view showing a configuration of a light irradiation apparatus according to an embodiment 6 of the present invention.

Based on FIG. 10, a configuration of the light irradiation apparatus 10 according to an embodiment 6 of the present invention will be described. FIG. 10 is a sectional view showing the configuration of the light irradiation apparatus 10 according to the embodiment 6.

As shown in FIG. 10, the light irradiation apparatus 10 according to the present embodiment is different from the light irradiation apparatus 10 of the embodiment 2 in that a substrate is covered to an end portion of the polymer gel layer 3. There was no big difference in the treatment effect itself, but in a case where the end portion is open, there is a case where the light beams leak out the outside from the end portion and sometimes dazzles, but in the present embodiment, this could be avoided.

In FIG. 10, the LED 4 is disposed at a part of the end portion. According to a configuration of the substrate 5, the LED 4 may be present at the end portion, and the treatment effect can be secured by prolonging the irradiation time even if the LED 4 may not be present.

Implementation Example with Software

A control block (current control apparatus 8) of the light irradiation apparatus 10 may be realized spy a logic circuit (hardware) formed in an integrated circuit (IC chip) or the like, or may be realized by a central processing unit (CPU) using software.

In the latter case, the light irradiation apparatus 10 Includes the CPU for performing instructions of a program which is software for realizing each function, a read only memory (ROM) in which the program and various types of pieces of data are recorded so as to be readable by a computer (or CPU) or a storage apparatus (this is referred to as "recording medium"), a random access memory (RAM) for developing the program, and the like. An object of the present invention is achieved by the computer (or CPU) reading the program from the recording medium and performing the program. As the recording medium, a "non-transitory tangible medium" such as a tape, a disk, a card, a semiconductor memory, and a programmable logic circuit can be used. In addition, the program may be supplied to the computer through an arbitrary transmission medium (communication network, broadcasting wave, or the like) capable of transmitting the program. The present invention can also be realized in a form of a data signal embedded in a carrier wave in which the program is embodied by electronic transmission.

Conclusion

The light irradiation apparatus 10 according to an aspect 1 of the present invention is the light irradiation apparatus that irradiates the treatment area 2 with the light beams, and includes a plurality of light-emitting diodes (LED 4) that generate the light beams and the polymer gel layer 3. The polymer gel layer 3 has a contact surface which directly or indirectly adheres to the treatment area 2, and is formed on the light-emitting diode with an approximately constant thickness.

By the configuration, despite the light irradiation apparatus 10 having a simple structure, there are the following advantages. That is, since the light-emitting diodes are arranged through the polymer gel layer 3, it is possible to irradiate the treatment area 2 with the light beams by covering the treatment area 2 having a curved surface. In addition, since the light-emitting diodes are arranged through the polymer gel layer 3 having an approximately constant thickness and irradiated, it is possible to uniformly irradiate the treatment area 2 with the light beams. Furthermore, since it is irradiated through the polymer gel layer 3 containing water, it is possible to suppress excessive heating by the light irradiation without excessive light irradiation.

In the light irradiation apparatus 10 according to an aspect 2 of the present invention, in the aspect 1, the light-emitting diodes are arranged at approximately even intervals, and the relationship of T/D≥½ may be established between the thickness T of the polymer gel layer 3 and the average distance D that is an average value of the distance between the adjacent light-emitting diodes.

With the configuration, since it is possible to set the thickness of the polymer gel layer 3 to an appropriate thickness that is not too thin with respect to the distance between the light-emitting diodes, it is possible to suppress occurrence of problems when the polymer gel layer 3 is too thin. That if the polymer gel layer 3 is thin, the light-emitting diode and the treatment area 2 become close to each other, and thus it is possible to suppress a problem that the treatment area 2 receives a large amount of light irradiation. In addition, if the thickness T is not kept uniform, the treatment area 2 close to the light-emitting diode receives a large amount of light irradiation. However, it is possible to suppress a problem that nonuniformity that the treatment area 2 away from the light-emitting diode receives only a small light irradiation occurs.

In the light irradiation apparatus 10 according to an aspect 3 of the present invention, in the aspect 1 or 2, the polymer gel holding layer 7 that is provided on the contact surface of the polymer gel layer 3 and passes through the light beams of a wavelength range used for the treatment may be provided.

With the configuration, since it is optically transparent with respect co the light beams of the wavelength range used for the treatment, it is possible to easily treat the polymer gel layer 3 without hindering irradiation by the light-emitting diode.

In the light irradiation apparatus 10 according to an aspect 4 of the present invention, in the aspects 1 to 3, the polymer gel layer 3 has the drug application portion 3a to which the drug is applied on the contact surface, or may contain the drug component.

With the configuration, a troublesome preparatory steps that the drug has to be taken before a certain time of treatment is not demanded. Furthermore, since the drug 21 can be directly applied on the treatment area 2, it is possible to deliver a high concentration of the drug to the treatment area, the effect of the drug does not reach an area other than the treatment area 2, side effects (for example, symptoms such as sunburn caused by action of drug and light) do not occur even if the light beams hits the portion, and the burden on the patient can be reduced. As described above, the configuration can be suitably used for the local treatment area 2.

In the light irradiation apparatus 10 according to an aspect 5 of the present invention, in the aspects 1 to 4, the energization control unit (current control apparatus 8) for controlling energization of the light-emitting diodes may be further provided so as to keep increase in a temperature of the polymer gel layer 3 within a certain temperature or less.

With the configuration, since a temperature does not exceed a certain temperature, it is possible to suppress the treatment area 2 being adversely affected by heat.

In the light irradiation apparatus 10 according to an aspect 6 of the present invention, in the aspects 1 to 5, the sensor 9 for monitoring at least one of the temperature of the treatment area 2 and the irradiation light intensity may be included.

With the configuration, the irradiation intensity can be controlled based on the temperature signal and the light amount signal from the sensor 9, and the irradiation can be stopped when reaching the demanded dose amount. In addition, by using the sensor 9, the light irradiation is interrupted so that the temperature does not exceed a predetermined temperature, and thus it is possible to suppress heating in the treatment area 2 and its surrounding skin 1.

In the light irradiation apparatus 10 according to an aspect 7 of the present invention, in the aspects 1 to 6, the polymer gel layer 3 may contain the light scattering body.

With the configuration, light scattering in the polymer gel layer 3 is increased, and thus it is possible to more uniform the light irradiation intensity.

In the light irradiation apparatus 10 according to an aspect 8 of the present invention, in the aspects 1 to 7, the plurality of substrates 51 having the same size is further provided, and at least one light-emitting diode may be mounted on each substrate.

With the configuration, even if there is an area where the treatment area 2 is not partially covered by the plurality of substrates 51 due to an optical confinement effect of the polymer gel layer 3, it is also possible to irradiate the area not covered with the light beams having sufficient intensity. The reason why such a plurality of substrates 51 can be used in combination is that the polymer gel layer 3 is interposed between the treatment area 2 and the substrates 51 to fix the treatment area 2 and the substrates 51 each other and to confine the light beams in order to equalize the irradiation intensity to some extent. Therefore, sufficient treatment can be performed by the light irradiation apparatus 10 having a simple structure without the cost of deforming the shape of the light-emitting diode or the like.

In the light irradiation apparatus 10 according to an aspect 9 of the present invention, in the aspects 1 to 8, the light-emitting diode protective layer for protecting the light-emitting diode may be provided or a protective case for accommodating the light-emitting diode may be provided.

With the structure, since the light-emitting diode is protected, problems such as corrosion and electric leakage can be suppressed.

The embodiments and examples disclosed herein are merely examples, and the present invention is not limited only to the above-described embodiments and examples. With reference to the description of the detailed description of the invention, the scope of the present invention is indicated by each claim of the claims, and includes meaning equivalent to and wording of the language described therein and all changes within the scope.

INDUSTRIAL APPLICABILITY

The present invention can mainly be used for the treatment and hairdressing for irradiating the light beams to the treatment area of human and animal skin.

REFERENCE SIGNS LIST 10 light irradiation apparatus
1 skin
2 treatment area
3 polymer gel layer
3a drug application portion
4 LED (light-emitting diode)
5 substrate
6 LED protective layer (light-emitting diode protective layer)

7 polymer layer
7a drug application portion
8 current control apparatus (energization control unit)
9 sensor
11 ceramic substrate
12 LED chip
13 bonding wire
14 resin dome
15 polyimide film
16 copper wire
17 silver plating
18 solder
19 die bond paste
20 resin layer
21 drug
22 light scattering body
51 substrate

The invention claimed is:

1. A light irradiation apparatus irradiating a treatment area with light beams, comprising:
    a flexible substrate;
    a wiring layer that is disposed on the flexible substrate;
    a plurality of light-emitting diodes which is connected to the wiring layer;
    a protective layer provided above the plurality of light-emitting diodes; and
    a polymer gel layer that contains water and is provided above the protective layer, wherein
    the flexible substrate, the wiring layer and the plurality of light-emitting diodes are covered with the protective layer,
    a surface of the protective layer covering the plurality of light-emitting diodes has a plurality of convex portions, and the plurality of convex portions is arranged so as to be installed inside the polymer gel layer such that the plurality of light-emitting diodes is received inside the polymer gel layer,
    the plurality of light-emitting diodes is disposed over a whole surface of the flexible substrate, wherein
    the polymer gel layer has a contact surface which directly or indirectly adheres to a treatment area, and is formed over the plurality of light-emitting diodes.

2. The light irradiation apparatus according to claim 1, further comprising a polymer gel holding layer that is provided on the contact surface of the polymer gel layer and causes the light beams in a wavelength range used for treatment to pass therethrough.

3. The light irradiation apparatus according to claim 1, wherein the polymer gel layer has a drug application portion, to which a drug is applied, on the contact surface, or contains a drug component.

4. The light irradiation apparatus according to claim 1, further comprising an energization control unit that controls energization of the plurality of light-emitting diodes so as to keep increase in temperature of the polymer gel layer within a certain temperature or less.

5. The light irradiation apparatus according to claim 1, further comprising: an optical sensor that measures an irradiation intensity at the treatment area of light emitted from the plurality of light-emitting diodes to the treatment area.

6. The light irradiation apparatus according to claim 5, further comprising: a control unit that calculates a dose amount of the light irradiated from the plurality of diodes to the treatment area based on the irradiation intensity measured by the optical sensor and irradiation time of the light emitted from the plurality of diodes, wherein the control unit controls the dose amount by controlling energization of the plurality of diodes.

7. The light irradiation apparatus according to claim 6, wherein the control unit terminates irradiation of the light from the plurality of the light emitted from the plurality of light-emitting diodes to the treatment area when the dose amount reaches a predetermined dose amount demanded for the treatment area.

8. The light irradiation apparatus according to claim 1, wherein the plurality of light-emitting diodes is arranged on a plane surface at approximately even intervals, and there is a relationship of $T/D \geq 1/2$ between a thickness T of the polymer gel layer and an average distance D that is an average value of distances between adjacent light-emitting diodes of the plurality of light-emitting diodes.

9. The light irradiation apparatus according to claim 1, wherein the plurality of light-emitting diodes is covered with a plurality of resin layers, respectively, and the plurality of resin layers is covered with the protective layer.

10. The light irradiation apparatus according to claim 1, wherein the plurality of light-emitting diodes is disposed at approximately even intervals.

11. The light irradiation apparatus according to claim 1, wherein the gel layer is formed with an approximately constant thickness.

* * * * *